United States Patent
Ohyama et al.

(10) Patent No.: US 9,933,430 B2
(45) Date of Patent: Apr. 3, 2018

(54) METHOD AND KIT FOR DISTINGUISHING BETWEEN PROSTATE CARCINOMA AND BENIGN PROSTATIC HYPERPLASIA

(71) Applicants: HIROSAKI UNIVERSITY, Hirosaki-shi (JP); Shizuoka Prefectural University Corporation, Shizuoka-shi (JP)

(72) Inventors: Chikara Ohyama, Hirosaki (JP); Tohru Yoneyama, Hirosaki (JP); Yuki Tobisawa, Hirosaki (JP); Shingo Hatakeyama, Hirosaki (JP); Takashi Suzuki, Shizuoka (JP); Ilpal Jwa, Shizuoka (JP); Maho Yamaguchi, Shizuoka (JP)

(73) Assignees: HIROSAKI UNIVERSITY, Hirosaki-shi (JP); SHIZUOKA PREFECTURAL UNIVERSITY CORPORATION, Shizuoka-shi (JP)

( * ) Notice: Subject to any disclaimer, the term of this patent is extended or adjusted under 35 U.S.C. 154(b) by 0 days.

(21) Appl. No.: 14/432,902

(22) PCT Filed: Oct. 9, 2013

(86) PCT No.: PCT/JP2013/077495
§ 371 (c)(1),
(2) Date: May 22, 2015

(87) PCT Pub. No.: WO2014/057983
PCT Pub. Date: Apr. 17, 2014

(65) Prior Publication Data
US 2015/0260720 A1  Sep. 17, 2015

(30) Foreign Application Priority Data
Oct. 12, 2012  (JP) .................. 2012-226489

(51) Int. Cl.
*G01N 33/574* (2006.01)
*C07K 16/18* (2006.01)

(52) U.S. Cl.
CPC .......... *G01N 33/57434* (2013.01); *G01N 2333/96433* (2013.01); *G01N 2400/02* (2013.01); *G01N 2400/12* (2013.01)

(58) Field of Classification Search
None
See application file for complete search history.

(56) References Cited

U.S. PATENT DOCUMENTS

| 6,258,540 B1 * | 7/2001 | Lo | .......... C12Q 1/6879 435/440 |
| 6,355,623 B2 * | 3/2002 | Seidman | .......... A61K 31/52 514/263.4 |
| 2004/0147033 A1 | 7/2004 | Shriver et al. | |
| 2006/0182682 A1 | 8/2006 | Ulmert | |
| 2009/0023220 A1 | 1/2009 | Amano et al. | |

FOREIGN PATENT DOCUMENTS

| CN | 101210927 A | 7/2008 | |
| EP | 2161571 A2 | 3/2010 | |
| EP | 2354790 A1 | 8/2011 | |
| EP | 2395357 A1 | 12/2011 | |
| JP | 2002-55108 A1 | 2/2002 | |
| JP | 2011-529184 A1 | 12/2011 | |
| WO | WO 2010/011357 A1 * | 1/2010 | .......... G01N 33/574 |
| WO | 2012001820 A1 | 1/2012 | |

OTHER PUBLICATIONS

Essentials of Glycobiology. 2nd edition. (Varki A, Cummings RD, Esko JD, et al., editors. Cold Spring Harbor (NY): Cold Spring Harbor Laboratory Press; 2009 Chapter 45—Cummings and Etzler).*
Trinkler et al. (Urology 1998 52(3): 479-486).*
Varki A, Cummings RD, Esko JD, et al., editors. (Essentials of Glycobiology. 2nd edition. Cold Spring Harbor (NY): Cold Spring Harbor Laboratory Press; 2009, Chapter 14—Varki and Schauer).*
Yoneyama et al. (European Urology Supplements Mar. 15, 2013 12 (1): e1042-e 043).*
Wako Jun'yaku Jiho (ISSN 1347-4804 Jan. 2012 80(1): 1-32).*
Wayback Machine (Wako Pure Chemicals, Anti-Sia alpha 2-3, Hyb4, Mar. 15, 2013, http://web.archive.org/web/20130315060525/http://www.wako-chem.co.jp/english/labchem/product/life/antiSia_a23/index.htm).*

(Continued)

*Primary Examiner* — Peter J Reddig
(74) *Attorney, Agent, or Firm* — Kratz, Quintos & Hanson LLP

(57) ABSTRACT

The method for distinguishing between prostate carcinoma and benign prostatic hyperplasia comprising: bringing an analyte sample containing a prostate-specific antigen (PSA) into contact with a carrier having an anti-free PSA antibody immobilized thereon, thereby binding free PSA to the anti-free PSA antibody immobilized on the carrier; thereafter bringing the carrier in which the free PSA is bound to the immobilized anti-free PSA antibody into contact with a monoclonal antibody capable of specifically recognizing a glycan in which a terminal sialic acid residue is bound to galactose through an α(2,3) bond, thereby binding the monoclonal antibody recognizing the glycan to the free PSA bound to the anti-free PSA antibody; measuring the amount of the free PSA having an N-type glycan in which a terminal sialic acid residue is bound to galactose through an α(2,3) bond; comparing the measured amount thus obtained with a preset cutoff value for prostate carcinoma and benign prostatic hyperplasia, thereby determining that when the measured amount is larger than the cutoff value, prostate carcinoma is developed or the probability of developing prostate carcinoma is high, and when the measured amount is smaller than the cutoff value, benign prostatic hyperplasia is developed or the probability of developing benign prostatic hyperplasia is high.

6 Claims, 3 Drawing Sheets

(56) References Cited

OTHER PUBLICATIONS

T. Kinoshita; "Tosa no Seibutsu Kino no Kaimei to Rio Gijutsu;" URL (http://www.jst.go.jp/kisoken/crest/report/heisei17/pdf/a10/f01/s013.pdf; 2005 (9 Sheets)/Cited in International Search Report.
S. Akimoto, et. al.; "Measurement of serum prostrate-specific antigen by DPC immulyze PSA kit and clinical evaluation in patients with prostrate cancer;" Hinyoki Geka; vol. 8; No. 10; Oct. 1995; pp. 939-943 (5 Sheets)/Cited in International Search Report.
International Search Report for International Application No. PCT/JP2013/077495 dated Nov. 5, 2013.
Tabares, Gloria et al., Different glycan structures in prostate-specific antigen from prostate cancer sera in relation to seminal plasma PSA, Glycobiology, 132-145, vol. 16, 2006, Oxford University Press, England (Advanced Access publication on Sep. 21, 2005).
Office Action of corresponding Chinese Patent Application No. 201380052947.0 dated Apr. 28, 2016.
Office Action of corresponding European Patent Application No. 13846084.5 dated May 3, 2016.

* cited by examiner

[Fig. 1]
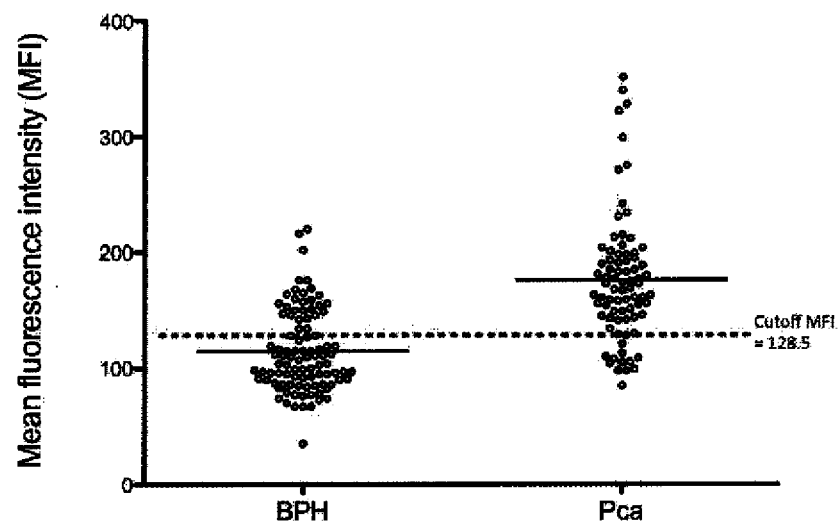
[Fig. 2]
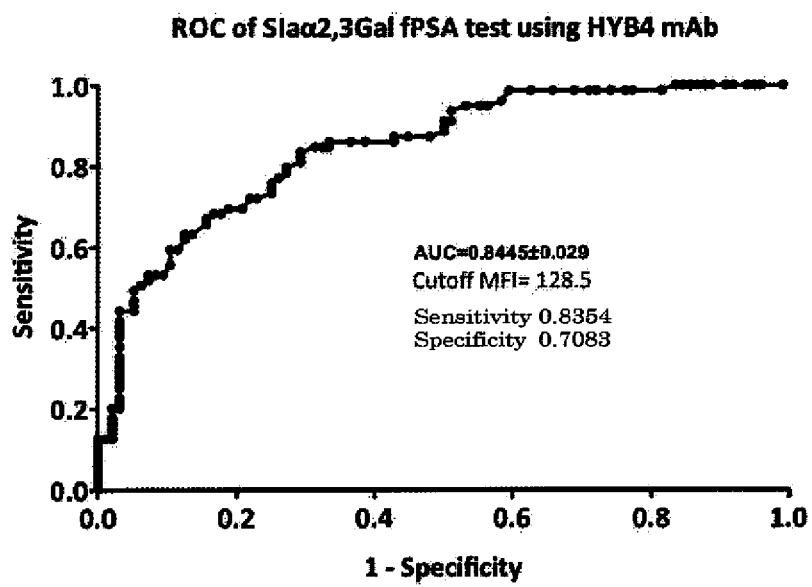

[Fig. 3]
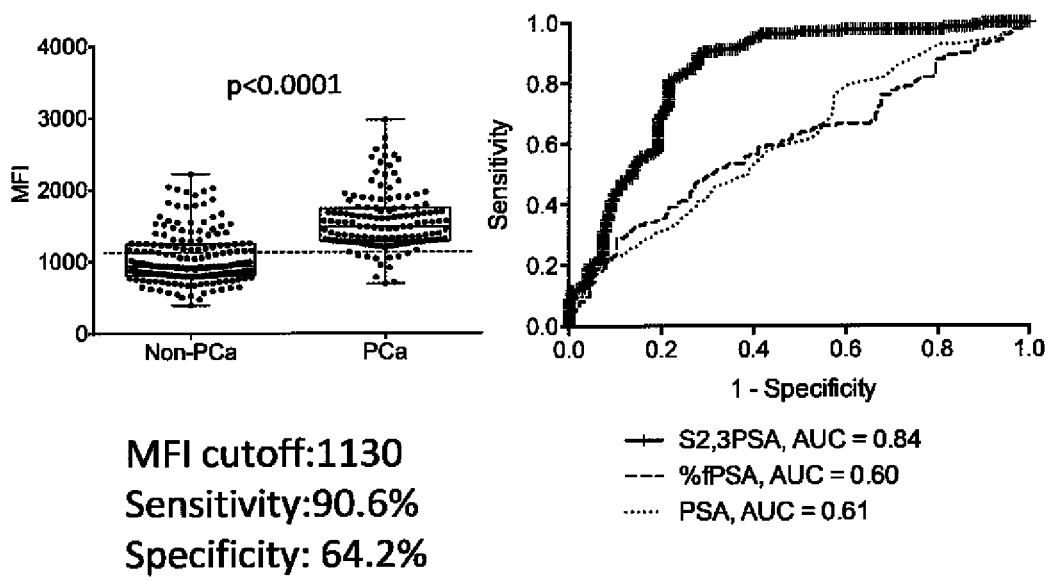
[Fig. 4]
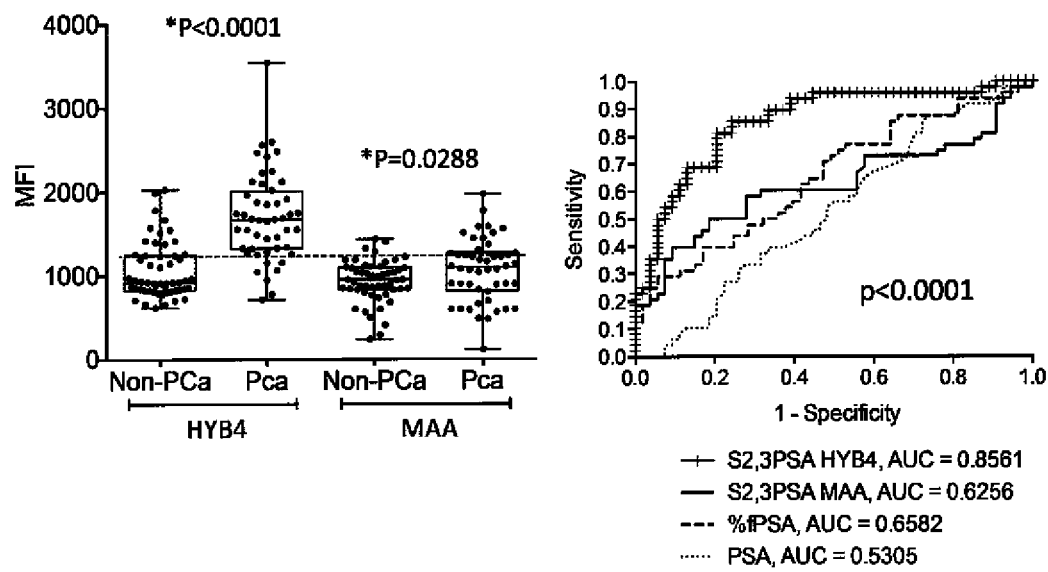

[Fig. 5]

The results obtained by calculating the value of "B (the measured value of fluorescence intensity of an analyte sample)/A", which is the ratio of the measured value, wherein A represents a mean fluorescence intensity (242) or a median fluorescence intensity (225) when the measurement was carried out for blank samples (left: A represents the mean fluorescence intensity, right: A represents the median fluorescence intensity).

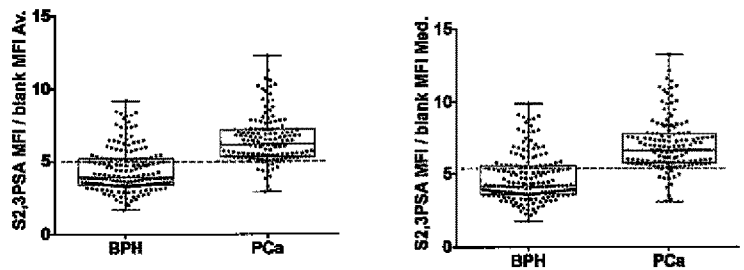

The results obtained by calculating the value of "B (the measured value of fluorescence intensity of an analyte sample)/A", which is the ratio of the measured value, wherein A represents a mean fluorescence intensity (228) or a median fluorescence intensity (215) when the measurement was carried out for HLT samples (left: A represents the mean fluorescence intensity, right: A represents the median fluorescence intensity).

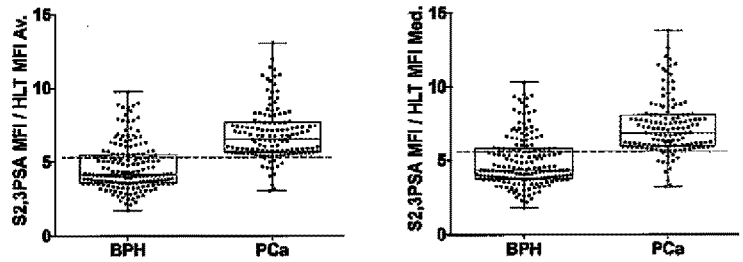

METHOD AND KIT FOR DISTINGUISHING BETWEEN PROSTATE CARCINOMA AND BENIGN PROSTATIC HYPERPLASIA

TECHNICAL FIELD

The present invention relates to a method and a kit for distinguishing between prostate carcinoma and benign prostatic hyperplasia.

BACKGROUND ART

As it has been well known that prostate carcinoma (hereinafter abbreviated as "Pca") is one of the leading causes of death of males, and a prostate-specific antigen (hereinafter abbreviated as "PSA") has been recognized as the most important tumor marker for Pca (Nonpatent Document 1). PSA is a glycoprotein of about 34 kDa and contains glycans in a proportion of about 8% thereof. The usefulness of a serum PSA test for the early diagnosis of Pca has already been described in many literatures. However, there is a region between males affected with Pca and males affected with benign prostate hyperplasia (hereinafter, abbreviated as "BPH") called a gray zone where Pca and BPH cannot be distinguished (Nonpatent Document 2). Therefore, attempts to accurately distinguish between these two pathologies, for example, attempts using a PSA density, a PSA gradient, the ratio of free PSA/total PSA, or the like as an index have been made. However, it is difficult to accurately distinguish between these two pathologies using such a method. Accordingly, the fact that a current serum PSA test is not specific to Pca and also does not have an appropriate cutoff value which satisfies both sensitivity and specificity has become a worldwide problem.

Under such a circumstance, a group including Ohyama, who is one of the present inventors, and others identified 19 types of glycans of PSA by treating PSA purified from seminal vesicle fluid with N-Glycosidase F, cleaving N-type glycans of PSA, and carrying out an analysis by matrix associated laser desorption/ionization time-of-flight (MALDI TOF) mass spectrometry (MS), and revealed that the glycans of PSA are very rich in diversity (Nonpatent Document 3). Prior to that, a group including Stamey and others has reported that as glycans of PSA, only an N-type glycan, which is composed of two strands, and in which sialic acid is bound at the terminal to galactose through an $\alpha(2,6)$ bond, is expressed (Nonpatent Document 4). However, it was revealed by the group including Ohyama and others that a glycan in which terminal sialic acid is bound to galactose through an $\alpha(2,3)$ bond is also present in a proportion of about 10% as well as a glycan in which terminal sialic acid is bound to galactose through an $\alpha(2,6)$ bond. After that, the group including Ohyama and others revealed that by analyzing PSA not only in a state of only glycans, but also in a state including a peptide sequence of PSA by MS-MS, a terminal sialic acid residue of an N-type glycan of PSA which is bound to galactose through an $\alpha(2,3)$ bond rather than through an $\alpha(2,6)$ bond increases with malignant transformation (Nonpatent Document 5).

In view of the above findings, it is considered that Pca and BPH can be distinguished from each other by using the amount of PSA having an N-type glycan in which a terminal sialic acid residue is bound to galactose through an $\alpha(2,3)$ bond as an index. In fact, it has been confirmed that Pca and BPH can be distinguished from each other by affinity chromatography using *Maackia amurensis* lectin capable of specifically recognizing a glycan in which a terminal sialic acid residue is bound to galactose through an $\alpha(2,3)$ bond, which has been proposed in Patent Document 1 by Ohyama who is one of the present inventors. The method for distinguishing between Pca and BPH by affinity chromatography using *Maackia amurensis* lectin has drawn attention as a method completely different from the methods which have been proposed so far. However, the method has a problem that a large amount (about 10 mL) of serum is required as an analyte sample for carrying out highly accurate discrimination because the amount of PSA having an N-type glycan in which a terminal sialic acid residue is bound to galactose through an $\alpha(2,3)$ bond is extremely small and is only 1 to 2% of the total PSA amount. Further, since *Maackia amurensis* lectin to be used is an extract from a natural product, the method also has a problem that a variation in quality is observed among lots.

PRIOR ART DOCUMENTS

Patent Documents

Patent Document 1: Japanese Patent No. 4514919

Nonpatent Documents

Nonpatent Document 1: Stamey T A, Yang N, Hay A R, et al., N. Engl. J. Med. 1987; 317: 909-916

Nonpatent Document 2: Catalona W J, et al., JAMA 1998; 279: 1542-1547

Nonpatent Document 3: Ohyama C, et al., Glycobiology, 2004; 14: 671-679

Nonpatent Document 4: Belanger A, Van Halbeek H, Gravuxes H C, et al. Prostate, 1995; 27: 187-197

Nonpatent Document 5: Tajiri M, Ohyama C, Wada Y, Glycobiology, 2008; 18: 2-8

SUMMARY OF THE INVENTION

Problems that the Invention is to Solve

Accordingly, an object of the present invention is to provide a method for distinguishing between Pca and BPH with high sensitivity and good reproducibility using a small amount of an analyte sample.

Means for Solving the Problems

As a result of intensive studies in view of the above points, the present inventors found that it is possible to distinguish between Pca and BPH with high sensitivity and good reproducibility using a small amount of an analyte sample by measuring the amount of free PSA having an N-type glycan in which a terminal sialic acid residue is bound to galactose through an $\alpha(2,3)$ bond contained in the analyte sample by means of an immunoassay using a monoclonal antibody capable of specifically recognizing a glycan in which a terminal sialic acid residue is bound to galactose through an $\alpha(2,3)$ bond.

A method for distinguishing between Pca and BPH of the present invention achieved based on the above-described finding comprises, as described in claim 1: bringing an analyte sample containing PSA into contact with a carrier having an anti-free PSA antibody immobilized thereon, thereby binding free PSA to the anti-free PSA antibody immobilized on the carrier; thereafter bringing the carrier in which the free PSA is bound to the immobilized anti-free PSA antibody into contact with a monoclonal antibody capable of specifically recognizing a glycan in which a terminal sialic acid residue is bound to galactose through an α(2,3) bond, thereby binding the monoclonal antibody capable of specifically recognizing a glycan in which a terminal sialic acid residue is bound to galactose through an α(2,3) bond to the free PSA bound to the anti-free PSA antibody immobilized on the carrier; measuring the amount of the free PSA having an N-type glycan in which a terminal sialic acid residue is bound to galactose through an α(2,3) bond; comparing the measured amount thus obtained with a preset cutoff value for Pca and BPH, thereby determining that when the measured amount is larger than the cutoff value, Pca is developed or the probability of developing Pca is high, and when the measured amount is smaller than the cutoff value, BPH is developed or the probability of developing BPH is high.

Further, the method described in claim 2 is a method in which the analyte sample containing PSA is at least one member selected from the group consisting of serum, urine, prostatic tissue extract, semen, and bladder irrigation fluid in the method described in claim 1.

Further, the method described in claim 3 is a method in which the anti-free PSA antibody is an anti-human free PSA-specific monoclonal antibody (which does not react with complexed PSA) in the method described in claim 1.

Further, the method described in claim 4 is a method in which the carrier is magnetic particles in the method described in claim 1.

Further, a kit for distinguishing between Pca and BPH of the present invention comprises, as described in claim 5, at least a carrier having an anti-free PSA antibody immobilized thereon and a monoclonal antibody capable of specifically recognizing a glycan in which a terminal sialic acid residue is bound to galactose through an α(2,3) bond.

Effect of the Invention

According to the present invention, a method for distinguishing between Pca and BPH with high sensitivity and good reproducibility using a small amount of an analyte sample can be provided.

BRIEF DESCRIPTION OF THE DRAWINGS

FIG. 1 It shows the measurement results of the amount of free PSA having an N-type glycan in which a terminal sialic acid residue is bound to galactose through an α(2,3) bond in the sera of Pca patients and BPH patients in Example 1 (based on fluorescence intensity).

FIG. 2 It shows ROC curves based on the above measurement results.

FIG. 3 It shows the measurement results of the amount of free PSA having an N-type glycan in which a terminal sialic acid residue is bound to galactose through an α(2,3) bond in the sera of Pca patients and BPH patients (left), and ROC curves based on the measurement results (right) in Example 2.

FIG. 4 It shows the measurement results of the amount of free PSA having an N-type glycan in which a terminal sialic acid residue is bound to galactose through an α(2,3) bond in the sera of Pca patients and BPH patients (left), and ROC curves based on the measurement results (right) in Example 3.

FIG. 5 It shows the measurement results of the amount of free PSA having an N-type glycan in which a terminal sialic acid residue is bound to galactose through an α(2,3) bond in the sera of Pca patients and BPH patients in Example 4 (corrected by the fluorescence intensity of blank samples or the fluorescence intensity of HLT samples).

MODE FOR CARRYING OUT THE INVENTION

The method for distinguishing between Pca and BPH of the present invention comprises: bringing an analyte sample containing PSA into contact with a carrier having an anti-free PSA antibody immobilized thereon, thereby binding free PSA to the anti-free PSA antibody immobilized on the carrier; thereafter bringing the carrier in which the free PSA is bound to the immobilized anti-free PSA antibody into contact with a monoclonal antibody capable of specifically recognizing a glycan in which a terminal sialic acid residue is bound to galactose through an α(2,3) bond, thereby binding the monoclonal antibody capable of specifically recognizing a glycan in which a terminal sialic acid residue is bound to galactose through an α(2,3) bond to the free PSA bound to the anti-free PSA antibody immobilized on the carrier; measuring the amount of the free PSA having an N-type glycan in which a terminal sialic acid residue is bound to galactose through an α(2,3) bond; comparing the measured amount thus obtained with a preset cutoff value for Pca and BPH, thereby determining that when the measured amount is larger than the cutoff value, Pca is developed or the probability of developing Pca is high, and when the measured amount is smaller than the cutoff value, BPH is developed or the probability of developing BPH is high.

In the present invention, examples of the analyte sample containing PSA include serum, urine, prostatic tissue extract, semen, and bladder irrigation fluid. The analyte sample may be prepared by a method known per se. The amount of the analyte sample may be small, and is preferably from 1 to 1000 μL, more preferably from 5 to 500 μL, most preferably from 10 to 100 μL.

The carrier having the anti-free PSA antibody immobilized thereon can be prepared by a method known per se using a commercially available anti-free PSA antibody and a commercially available carrier. In order to measure the amount of free PSA having an N-type glycan in which a terminal sialic acid residue is bound to galactose through an α(2,3) bond with high sensitivity, it is preferred to use an anti-human free PSA-specific monoclonal antibody (which does not react with complexed PSA) as the anti-free PSA antibody (for example, an antibody derived from clone 2E2, an antibody derived from clone 8A6, and the like are commercially available). The carrier may be any as long as the antibody can be immobilized thereon such as magnetic particles or a well plate. Magnetic particles, however, are preferred in that they can be easily collected by a magnetic force, and therefore, the handleability thereof is excellent. Incidentally, the "free PSA" as used herein refers to PSA which is not bound to a protein such as α1-antichymotrypsin, and is also called "PSA in the protein-unbound form" or "PSA in the free form" (the "complexed PSA" refers to PSA which is bound to a protein).

The monoclonal antibody capable of specifically recognizing a glycan in which a terminal sialic acid residue is bound to galactose through an α(2,3) bond may be any as long as it is a monoclonal antibody capable of specifically recognizing a glycan in which a terminal sialic acid residue is bound to galactose through an α(2,3) bond, that is, a Siaα(2,3) Gal glycan. Examples of the commercially available monoclonal antibody include an HYB4 monoclonal antibody (Wako Pure Chemical Industries, Ltd.) established by a group including Suzuki, who is one of the present inventors, and others, but it is not limited thereto.

Both of the step of bringing an analyte sample containing PSA into contact with a carrier having an anti-free PSA antibody immobilized thereon, thereby binding free PSA to the anti-free PSA antibody immobilized on the carrier, and the step of bringing the carrier in which the free PSA is bound to the immobilized anti-free PSA antibody into contact with a monoclonal antibody capable of specifically recognizing a glycan in which a terminal sialic acid residue is bound to galactose through an α(2,3) bond, thereby binding the monoclonal antibody capable of specifically recognizing a glycan in which a terminal sialic acid residue is bound to galactose through an α(2,3) bond to the free PSA bound to the anti-free PSA antibody immobilized on the carrier may be carried out, for example, under the temperature conditions of 2° C. to 5° C. for 10 minutes to 3 hours. The measurement of the amount of free PSA having an N-type glycan in which a terminal sialic acid residue is bound to galactose through an α(2,3) bond can be carried out by, for example, a sandwich ELISA (Enzyme-Linked Immunosorbent Assay) method or a flow cytometry method. In the latter case, the measurement may be carried out, for example, using a secondary antibody labeled with a fluorescence which can be detected, but can also be carried out by fluorescently labeling the monoclonal antibody capable of specifically recognizing a glycan in which a terminal sialic acid residue is bound to galactose through an α(2,3) bond without using a secondary antibody. Incidentally, the label for the antibody may be any as long as it can be detected, and is not limited to a fluorescent label. It goes without saying that an operation such as washing, purification, or fractionation may be carried out at the time of measurement as needed. Further, the carrier having an anti-free PSA antibody immobilized thereon and the monoclonal antibody capable of specifically recognizing a glycan in which a terminal sialic acid residue is bound to galactose through an α(2,3) bond may come in a kit along with a washing liquid or the like so that it is possible to easily and simply distinguish between Pca and BPH.

By comparing the thus measured amount of free PSA having an N-type glycan in which a terminal sialic acid residue is bound to galactose through an α(2,3) bond with a preset cutoff value for Pca and BPH, it can be determined that when the measured amount is larger than the cutoff value, Pca is developed or the probability of developing Pca is high, and when the measured amount is smaller than the cutoff value, BPH is developed or the probability of developing BPH is high. The cutoff value can be set based on the measured value in a group of males affected with Pca and the measured value in a group of males affected with BPH. For example, in the case where the measurement is carried out using a fluorescent label, the cutoff value can be set to a numerical value within the range from 1 to 10000 as a fluorescence intensity (MFI: Mean Fluorescence Intensity) according to the measurement conditions, etc.

EXAMPLES

Hereinafter, the present invention will be described in detail with reference to Examples, however, the present invention is not construed as being limited to the following description.

Reference Example 1

Production of HYB4 Monoclonal Antibody Capable of Specifically Recognizing Glycan in which Terminal Sialic Acid Residue is Bound to Galactose Through α(2,3) Bond A monoclonal antibody capable of specifically recognizing a glycan in which a terminal sialic acid residue is bound to galactose through an α(2,3) bond to be used for distinguishing between prostate carcinoma and benign prostatic hyperplasia in the present invention was produced according to the following procedure.

(1) Preparation of Antigen

IV$^3$NeuAcnLc$_4$Cer (NeuAcα2-3Galβ1-4GlcNAcβ1-3Galβ1-4Glcβ1-1'Cer), which is a glycolipid, was used as an immunogen.

(1) Preparation of Hybridoma

228 μg of IV$^3$NeuAcnLc$_4$Cer (NeuAcα2-3Galβ1-4GlcNAcβ1-3Galβ1-4Glcβ1-1'Cer) was dissolved in 114 μL of EtOH, and the resulting solution was treated by sonication. Then, 1820 μL of PBS was added thereto, and the resulting solution was heated to 37° C. Thereafter, 568 μL of a solution in which a *Salmonella* minnesota bacterial membrane fraction treated with an acid was suspended in PBS at 1 mg/mL was added thereto as an adjuvant, and the resulting mixed solution was left to stand at 37° C. for 10 minutes. Then, a 200 μL aliquot of this mixed solution was administered to the tail vein of a C3H mouse on days 0, 4, 7, 11, 21, and 25. On day 3 after the final administration, lymphocytes prepared from the spleen of the immunized mouse were subjected to cell fusion according to the common procedure of Kohler and Milstein (Nature, 256, 495, 1975). As a parent cell serving as a fusion partner, PAI (Health Science Research Resources Bank, JCRB0113), which is a mouse myeloma cell line, was used, and as a fusion agent, polyethylene glycol 4000 (Merck KGaA) was used. The thus fused cells were suspended in HAT medium, and the suspension was dispensed in a 96-well microculture plate, followed by incubation. After about 2 weeks, screening for the production of the antibody in the culture supernatant in colony positive wells was carried out by an ELISA method using IV$^3$NeuAcnLc$_4$Cer as an antigen. The screening was carried out as follows using a 96-well microtiter plate (Dynatech Laboratories, Inc., IMMULON 1B). IV$^3$NeuAcnLc$_4$ Cer was prepared at 0.1 nmol/50 μL with 95% EtOH, and added to the 96-well microtiter plate at 50 μL/well. To the well to serve as a blank, 50 μl of 95% EtOH was added. EtOH was evaporated under reduced pressure, thereby immobilizing the glycolipid antigen on the well, and PBS containing 1% human serum albumin (Sigma-Aldrich Co., A6784) (PBS-1) was added thereto at 20 μL/well, and then, the plate was left at room temperature for 1 hour. After PBS-1 was removed, the hybridoma culture supernatant was added thereto at 50 μL/well, and a reaction was allowed to proceed at room temperature for 1 hour. After the culture supernatant was removed, each well was washed once with PBS at 100 μL/well. A secondary antibody (Protein A-HRP) solution obtained by dilution of the secondary antibody to 10000 fold with PBS-1 was added thereto at 100 μL/well, and a reaction was allowed to proceed at room temperature for 1 hour. After the secondary antibody solution was removed, each well was washed 5 times with PBS at 100 μL/well. Then, a peroxidase substrate (a solution obtained by dissolving 2 mg of O-phenylenediamine with 5 mL of 80 mM citrate-phosphate buffer (pH 5.6) and 2 μL of 30% hydrogen peroxide) was added thereto at 100 μL/well. The plate was left under light shielding conditions, and when color development was observed, the color development was stopped by adding 1 M HCl at 100 μL. Thereafter, an absorbance was measured using a microplate reader by setting the measurement wavelength to 492 nm and the control wavelength to 630 nm. Three hybridoma clones having a high antibody-producing ability and a good growth potential were obtained (an antibody production-positive rate: 0.5%). The classes of the antibodies produced by the obtained clones were all IgG3 (κ). Among the hybridomas screened as described above, a monoclonal antibody derived from clone HYB4 specifically reacted with a Siaα(2,3)Gal glycan.

(3) Preparation of HYB4 Monoclonal Antibody

The hybridoma (clone HYB4) obtained in (2) was pre-cultured for 2 days using a 75 cm$^2$ flask (CORNING Incorporated, 430720) in 25 mL of RPMI 1640 medium (Nissui Pharmaceutical Co., Ltd., 05918) containing 10% (v/v) Fetal bovine serum (FBS) at 37° C. in the presence of 5% $CO_2$. The cells were collected from two 75 cm$^2$ flasks and suspended in 1 L of E-RDF medium (Kyokuto Pharmaceutical Industrial Co., Ltd., 26500), and then, the resulting suspension was transferred to amass culture apparatus (spinner flask), and rotation culture was carried out at 37° C. for 4 days. In this culture solution, the monoclonal antibody which specifically reacts with a Siaα(2,3)Gal glycan was contained at a high concentration. The culture solution derived from the clone HYB4 was purified by affinity chromatography using Protein A Sepharose. The HYB4 monoclonal antibody thus prepared from the hybridoma (clone HYB4) was characterized in that the type of immunoglobulin was IgG3, and the molecular weight was about 150,000 Da. The thus established HYB4 monoclonal antibody is commercially available from Wako Pure Chemical Industries, Ltd.

Example 1

Discrimination Between Pca and BPH Using HYB4 Monoclonal Antibody (1)

The discrimination between Pca and BPH using the HYB4 monoclonal antibody was carried out according to the following procedure.

(1) Immobilization of Anti-free PSA Antibody on Carrier

Magplex microsphere (Luminex Corporation), which is magnetic beads, was used as a carrier, and an anti-free PSA antibody was immobilized on the surface thereof according to a manual accompanying the XMAP Antibody Coupling Kit. Specifically, Magplex microsphere was added to a 1.5 mL tube at 6.25×10$^6$ microspheres/500 μL, and the tube was left to stand on Magnetic Separator for 2 minutes. After the magnetic beads were precipitated, the supernatant was sucked off. 500 μL of Activation buffer was added to the tube, followed by mixing for 10 seconds, and the tube was left to stand on Magnetic Separator for 2 minutes. After the magnetic beads were precipitated, the supernatant was sucked off. 400 μL of Activation buffer was added to the tube again, followed by mixing for 10 seconds. Subsequently, 50 μL of Sulfo-NHS and 50 μL of an EDC solution were added thereto, followed by mixing for 10 seconds, and the resulting mixture was left at room temperature for 20 minutes. Then, the tube was left to stand on Magnetic Separator for 2 minutes. After the magnetic beads were precipitated, the supernatant was sucked off. In order to wash the magnetic beads, 500 μL of Wash buffer was added thereto, followed by mixing for 10 seconds, and the tube was left to stand on Magnetic Separator for 2 minutes. After the magnetic beads were precipitated, the supernatant was sucked off. This washing operation was repeated 3 times in total. 25 μg of an anti-human free PSA-specific monoclonal antibody (an anti-free PSA antibody which is derived from clone 2E2, and does not react with complexed PSA) (Funakoshi Co., Ltd.) was mixed with 1000 μL of Activation buffer, and the resulting mixture was added to the tube containing the magnetic beads. The tube was left at room temperature for 2 hours while gently mixing (at 15 to 30 rpm). Then, the tube was left to stand on Magnetic Separator for 2 minutes. After the magnetic beads were precipitated, the supernatant was sucked off. In order to wash the magnetic beads, 500 μL of Wash buffer was added thereto, followed by mixing for 10 seconds, and the tube was left to stand on Magnetic Separator for 2 minutes. After the magnetic beads were precipitated, the supernatant was sucked off. This washing operation was repeated 3 times in total. Finally, 1 mL of Wash buffer was added thereto, whereby Magplex microsphere having the anti-free PSA antibody immobilized thereon were prepared at 6250 microspheres/μL and stored at 4° C. until use.

(2) Quantitative Determination of Free PSA Having N-type Glycan in which Terminal Sialic Acid Residue is Bound to Galactose Through α(2,3) Bond Using Luminex System (A) Subjects for Quantitative Determination The subjects consisted of 79 Pca patients and 96 BPH patients having a total PSA level of 20.0 ng/mL or less, and the serum was collected from each patient, and the measurement was carried out. The histopathological diagnosis of the patients was confirmed by carrying out prostate biopsy. The age, PSA level, histopathological malignancy grade, and clinical stage of the patients are shown in Table 1.

TABLE 1

|  | BPH | Pca | p-value |
| --- | --- | --- | --- |
| Number of patients | 96 | 79 |  |
| Age (median) | 69.5 ± 8.0 | 72.0 ± 7.3 | 0.2634 |
| Total PSA level (ng/mL) | 2.1-19.7 | 3.0-17.6 | 0.1421 |
| Median total PSA level | 6.60 | 7.5 |  |
| 0-4 ng/mL (%) | 2.1 | 2.5 |  |
| 4-10 ng/mL (%) | 78.1 | 69.6 |  |
| 10-20 ng/mL (%) | 19.7 | 27.8 |  |
| >20 ng/mL (%) | 0 | 0 |  |
| Gleason score |  |  |  |
| GS 6 (%) | — | 3.3 |  |
| GS 7 (%) | — | 43.3 |  |
| GS 8 (%) | — | 18.3 |  |
| GS 9 (%) | — | 35 |  |
| GS 10 (%) | — | 0 |  |
| cT stage (clinical tumor size) |  |  |  |
| T1c-T2a (%) | — | 75.9 |  |
| T2b (%) | — | 7.6 |  |
| T2c-T3 (%) | — | 13.9 |  |
| T4 | — | 0 |  |

(B) Quantitative Determination Method

To each well of a white 96-well plate (Whatman Inc.), the Magplex microsphere having the anti-free PSA antibody immobilized thereon prepared in (1) were added at 12500 microspheres/2 μL. After 50 μL of Carbofree Blocking buffer (Funakoshi Co., Ltd.) was added to each well to block the magnetic beads, 20 μL of the serum which is an analyte sample was added to each well, and the plate was left at 4° C. for 1 hour. Then, the magnetic beads were washed 3 times with 100 μL of Tris-buffered saline containing 0.01% Tween 20 (TBST). Subsequently, 50 μL of the HYB4 monoclonal antibody was mixed in each well, and the plate was left at 4° C. for 1 hour. After the magnetic beads were washed 3 times with 50 μL of TBST, 50 μL of a Phycoerythrin fluorescent dye (PE)-labeled anti-mouse IgG3 antibody (Santa Cruz Biotechnology, Inc.) was mixed in each well, and the plate was left at room temperature for 45 minutes. The white 96-well plate was placed in Luminex 100 flow-metry, and the fluorescence intensity (MFI: Mean Fluorescence Intensity) of each well was measured.

C) Results of Quantitative Determination

The results of the quantitative determination are shown in FIG. 1. As apparent from FIG. 1, the fluorescence intensity of the sera of the Pca patients was significantly higher than the fluorescence intensity of the sera of the BPH patients ($P<0.001$, Mann Whitney U-test). That is, this means that the amount of free PSA having an N-type glycan in which a terminal sialic acid residue is bound to galactose through an $\alpha(2,3)$ bond in the serum of the Pca patient is larger than that in the serum of the BPH patient. Further, based on the results of the quantitative determination, a Relative Operating Characteristic curve (ROC curve) analysis was carried out. As a result, it was found that the MFI cutoff value was 128.5, the sensitivity was 0.8354, the specificity was 0.7083, and the AUC (Area Under the Curve) was 0.8445 (FIG. 2).

(3) Discrimination Between Pca and BPH

When Pca and BPH were distinguished by the method of the present invention based on the MFI cutoff value set in (2), about 75% (73 patients) of the patients (98 patients) who were diagnosed with BPH by carrying out needle biopsy for the patients (177 patients) diagnosed with suspected Pca based on a conventional PSA test could be determined to be affected with BPH. From the above results, it was found that it is possible to distinguish between Pca and BPH with high sensitivity and good reproducibility using a small amount of an analyte sample according to the present invention. In a currently conducted serum PSA test as a diagnostic method for Pca, it is difficult to distinguish between Pca and BPH, and in the case where the PSA level is 4 ng/mL or more, it is necessary to carry out biopsy in which a needle is inserted into the prostate gland. However, the current situation is that the percentage of patients who undergo needle biopsy and are diagnosed with Pca is merely about 20%, and therefore, the remaining about 80% of the patients have to undergo needle biopsy which is originally unnecessary. Moreover, needle biopsy is an invasive procedure, and therefore there is a concern that it may come with a serious adverse event such as bleeding or infection. According to the present invention, it is possible to distinguish between Pca and BPH with high sensitivity and good reproducibility using a small amount of an analyte sample, and therefore, cases required to carry out needle biopsy can be narrowed down, and thus, noninvasive diagnosis for Pca, which has been difficult so far, can be carried out.

Example 2

Discrimination Between Pca and BPH Using HYB4 Monoclonal Antibody (2)

The discrimination between Pca and BPH using the HYB4 monoclonal antibody was carried out according to the following procedure.

(1) Immobilization of Anti-free PSA Antibody on Carrier

Magplex microsphere (Luminex Corporation), which is magnetic beads, was used as a carrier, and an anti-free PSA antibody was immobilized on the surface thereof according to a manual accompanying the XMAP Antibody Coupling Kit. Specifically, Magplex microsphere was added to a 1.5 mL tube at $1.25 \times 10^7$ microspheres/1000 µL, and the tube was left to stand on Magnetic Separator for 2 minutes. After the magnetic beads were precipitated, the supernatant was sucked off. 500 µL of Activation buffer was added to the tube, followed by mixing for 10 seconds, and the tube was left to stand on Magnetic Separator for 2 minutes. After the magnetic beads were precipitated, the supernatant was sucked off. 400 µL of Activation buffer was added to the tube again, followed by mixing for 10 seconds. Subsequently, 50 µL of Sulfo-NHS and 50 µL of an EDC solution were added thereto, followed by mixing for 10 seconds, and the resulting mixture was left at room temperature for 20 minutes. Then, the tube was left to stand on Magnetic Separator for 2 minutes. After the magnetic beads were precipitated, the supernatant was sucked off. In order to wash the magnetic beads, 500 µL of Wash buffer was added thereto, followed by mixing for 10 seconds, and the tube was left to stand on Magnetic Separator for 2 minutes. After the magnetic beads were precipitated, the supernatant was sucked off. This washing operation was repeated 3 times in total. 62.5 jag of an anti-human free PSA-specific monoclonal antibody (an anti-free PSA antibody which is derived from clone 8A6, and does not react with complexed PSA) (Abcam plc) was mixed with 500 µL of Activation buffer, and the resulting mixture was added to the tube containing the magnetic beads. The tube was left at room temperature for 2 hours while gently mixing (at 15 to 30 rpm). Then, the tube was left to stand on Magnetic Separator for 2 minutes. After the magnetic beads were precipitated, the supernatant was sucked off. In order to wash the magnetic beads, 500 µL of Wash buffer was added thereto, followed by mixing for 10 seconds, and the tube was left to stand on Magnetic Separator for 2 minutes. After the magnetic beads were precipitated, the supernatant was sucked off. This washing operation was repeated 3 times in total. Finally, 2 mL of Wash buffer was added thereto, whereby Magplex microsphere having the anti-free PSA antibody immobilized thereon were prepared at 6250 microspheres/µL and stored at 4° C. until use.

(2) Quantitative Determination of Free PSA Having N-type Glycan in which Terminal Sialic Acid Residue is Bound to Galactose Through $\alpha(2,3)$ Bond Using Luminex System (A) Subjects for Quantitative Determination The subjects consisted of 138 Pca patients and 176 BPH patients having a total PSA level of 10.0 ng/mL or less, and the serum was collected from each patient, and the measurement was carried out. The histopathological diagnosis of the patients was confirmed by carrying out prostate biopsy. The age, PSA level, histopathological malignancy grade, and clinical stage of the patients are shown in Table 2 (in the table, "Non-PCa" denotes the BPH patients).

TABLE 2

| Characteristics | Non-PCa | PCa | P |
|---|---|---|---|
| Patients (n) | 176 | 138 | |
| Median Age (range) | 68.0 (51-83) | 69.0 (50-84) | 0.0181 |
| Median PSA, ng/mL (range) | 5.8 (2.0-10.0) | 6.4 (2.2-10.0) | 0.0008 |
| Median fPSA, ng/mL (range) | 0.12 (0-2.43) | 0.10 (0-4.40) | 0.1267 |
| Median % fPSA (%, range) | 2.1 (0-51.6) | 1.6 (0-44.0) | 0.0020 |
| Median S2,3PSA, MFI (range) | 940 (395-2221) | 1484 (693-2971) | <0.0001 |
| Biopsy Gleason Sum, n (%) | | | |
| 5-6 | | 24 (17.5) | |
| 7 | | 66 (48.2) | |
| 8-10 | | 48 (34.3) | |

TABLE 2-continued

| Characteristics | Non-PCa | PCa | P |
|---|---|---|---|
| Clinical stage (n, %) | | | |
| cT1c-cT2a | | 127 (92.0) | |
| cT2b | | 3 (2.2) | |
| cT2c | | 7 (5.1) | |
| unknown | | 1 (0.7) | |
| D'Amico Risk category (n, %) | | | |
| low | | 24 (17.4) | |
| intermediate | | 64 (46.4) | |
| high | | 50 (36.2) | |

(B) Quantitative Determination Method

The quantitative determination was carried out in the same manner as described in Example 1.

(C) Results of Quantitative Determination

The results of the quantitative determination are shown on the left of FIG. 3 (in the drawing, "Non-PCa" denotes the BPH patients). As apparent from the diagram on the left of FIG. 3, the fluorescence intensity of the sera of the Pca patients was significantly higher than the fluorescence intensity of the sera of the BPH patients (P<0.0001, Mann Whitney U-test). That is, this means that the amount of free PSA having an N-type glycan in which a terminal sialic acid residue is bound to galactose through an α(2,3) bond in the serum of the Pca patient is larger than that in the serum of the BPH patient. Further, based on the results of the quantitative determination, a Relative Operating Characteristic curve (ROC curve) analysis was carried out. As a result, it was found that the MFI cutoff value was 1130, the sensitivity was 90.6%, the specificity was 64.2%, and the AUC was 0.84 (on the right of FIG. 3: S2,3PSA). On the other hand, according to a total PSA measurement method, the AUC was 0.61, and according to a percent free PSA measurement method (a method using the ratio of the free PSA to the total PSA as an index), the AUC was 0.60 (on the right of FIG. 3: in the drawing, "PSA" denotes the total PSA measurement method, and "% fPSA" denotes the percent free PSA measurement method). Accordingly, the results that the method of the present invention has the sensitivity of 90% or more and the AUC of 0.80 or more supported that the method of the present invention has high discrimination accuracy between Pca and BPH. The results of comparison of specificity, diagnostic accuracy, positive diagnosis rate, and negative diagnosis rate with respect to the method of the present invention, the total PSA measurement method, and the percent free PSA measurement method are shown in Table 3 (in the table, "S2,3PSA" denotes the method of the present invention, "PSA" denotes the total PSA measurement method, and "% fPSA" denotes the percent free PSA measurement method). As apparent from Table 3, it was found that according to the method of the present invention, it is possible to distinguish between Pca and BPH with the specificity of 60% or more, the diagnostic accuracy of 70% or more, the positive diagnosis rate of 60% or more, and the negative diagnosis rate of 80% or more.

TABLE 3

| | S2,3PSA, | PSA | % fPSA |
|---|---|---|---|
| Cutoff values normalized by sensitivity for S2,3PSA test | >1130 (MFI) | >4.5 ng/mL | <5.39% |
| Sensitivity (%) | 90.6 | 90.6 | 90.6 |
| Specificity (%) | 64.2 | 9.7 | 11.9 |
| Accuracy (%) | 75.8 | 45.2 | 46.5 |
| Positive predictive value (%) | 66.5 | 44.0 | 44.6 |
| Negative predictive value (%) | 89.7 | 56.7 | 61.8 |

Example 3

Comparison of Discrimination Between Pca and BPH Using HYB4 Monoclonal Antibody with Discrimination Between Pca and BPH Using *Maackia amurensis* Lectin The comparison of discrimination between Pca and BPH using the HYB4 monoclonal antibody with discrimination between Pca and BPH using *Maackia amurensis* lectin was carried out according to the following procedure.

(1) Immobilization of Anti-free PSA Antibody on Carrier

The immobilization of an anti-free PSA antibody on a carrier was carried out in the same manner as described in Example 2.

(2) Quantitative Determination of Free PSA Having N-type Glycan in which Terminal Sialic Acid Residue is Bound to Galactose Through α(2,3) Bond Using Luminex System (A) Subjects for Quantitative Determination The subjects consisted of 48 Pca patients and 54 BPH patients having a total PSA level of 20.0 ng/mL or less, and the serum was collected from each patient, and the measurement was carried out. The histopathological diagnosis of the patients was confirmed by carrying out prostate biopsy. The age, PSA level, histopathological malignancy grade, and clinical stage of the patients are shown in Table 4 (in the table, "Non-PCa" denotes the BPH patients).

TABLE 4

| Characteristics | Non-PCa | PCa | P |
|---|---|---|---|
| Patients (n) | 54 | 48 | |
| Median Age (range) | 69.0 (53-81) | 72.5 (58-84) | 0.0737 |
| Median PSA (ng/mL, range) | 6.65 (2.4-17.1) | 7.10 (3.1-15.3) | 0.5989 |
| Median fPSA (ng/mL, range) | 0.23 (0.05-1.09) | 0.16 (0.00-0.69) | 0.0166 |
| Median % fPSA (%, range) | 3.00 (0.84-18.7) | 2.24 (0.14-9.02) | 0.0083 |
| Median S2,3PSA HYB4 (MFI, range) | 922 (621-2030) | 1670 (716-3545) | <0.0001 |
| Median S2,3PSA MAA (MFI, range) | 953 (239-1436) | 1095 (118-1970) | 0.0288 |
| Biopsy Gleason Sum (n, %) | | | |
| 5-6 | | 0 (0) | |
| 7 | | 26 (54.2) | |
| 8-10 | | 22 (45.8) | |

TABLE 4-continued

| Characteristics | Non-PCa | PCa | P |
|---|---|---|---|
| Clinical stage (n, %) | | | |
| cT1c-cT2a | | 39 (81.25) | |
| cT2b | | 3 (6.25) | |
| cT2c-cT3 | | 6 (12.5) | |
| D'Amico Risk category (n, %) | | | |
| low | | 0 (0) | |
| intermediate | | 23 (47.9) | |
| high | | 25 (52.1) | |

(B) Quantitative Determination Method
(i) In the Case of Using HYB4 Monoclonal Antibody The quantitative determination was carried out in the same manner as described in Example 1.

(ii) In the Case of using *Maackia amurensis* Lectin

To each well of a white 96-well plate (Whatman Inc.), the Magplex microsphere having the anti-free PSA antibody immobilized thereon prepared in (1) were added at 12500 microspheres/2 μL. After 50 μL of Carbofree Blocking buffer (Funakoshi Co., Ltd.) was added to each well to block the magnetic beads, 20 μL of the serum which is an analyte sample was added to each well, and the plate was left at 4° C. for 1 hour. Then, the magnetic beads were washed 3 times with 100 μL of Tris-buffered saline containing 0.01% Tween 20 (TBST). Subsequently, 50 μL of biotin-labeled *Maackia amurensis* lectin (Biotinylated MAA: Vector Laboratories, Inc.) was mixed in each well, and the plate was left at 4° C. for 1 hour. After the magnetic beads were washed 3 times with 50 μL of TBST, 50 μL of a Phycoerythrin fluorescent dye (PE)-labeled streptavidin (Santa Cruz Biotechnology, Inc.) was mixed in each well, and the plate was left at room temperature for 45 minutes. The white 96-well plate was placed in Luminex 100 flowmetry, and the fluorescence intensity (MFI) of each well was measured.

(C) Results of Quantitative Determination

The results of the quantitative determination are shown on the left of FIG. 4 (in the drawing, "Non-PCa" denotes the BPH patients, "HYB4" denotes the method of the present invention, and "MAA" denotes the method using *Maackia amurensis* lectin). As apparent from the diagram on the left of FIG. 4, according to the method of the present invention, a difference between the fluorescence intensity of the serum of the Pca patient and the fluorescence intensity of the serum of the BPH patient could be recognized using the serum in an amount as small as 20 but could not be recognized by the method using *Maackia amurensis* lectin. Further, based on the results of the quantitative determination, a Relative Operating Characteristic curve (ROC curve) analysis was carried out. As a result, as apparent from the diagram on the right of FIG. 4, the method of the present invention had the AUC of 0.8561 (S2,3PSA HYB4). On the other hand, the method using *Maackia amurensis* lectin had the AUC of 0.6256 (S2,3PSA MAA), which was not much different from the AUC (0.5305: PSA) of the total PSA measurement method or the AUC (0.6582: % fPSA) of the percent free PSA measurement method. Accordingly, it was found that the method of the present invention has high discrimination accuracy between Pca and BPH even if a small amount of an analyte sample is used as compared with the method using *Maackia amurensis* lectin.

Example 4

Setting of Cutoff Value for Distinguishing Between Pca and BPH Using HYB4 Monoclonal Antibody In order to normalize the cutoff value for distinguishing between Pca and BPH in the method of the present invention in Example 2, the cutoff value was expressed as a ratio obtained by dividing the fluorescence intensity of the serum which is an analyte sample by the fluorescence intensity measured in the same manner as described in Example 2 with respect to samples which did not contain the serum of 27 cases (blank samples: phosphate buffer) or the sera of normal subjects of 80 cases (HLT samples). The results are shown in FIG. 5. As apparent from FIG. 5, since in the HLT sample, free PSA having an N-type glycan in which a terminal sialic acid residue is bound to galactose through an α(2,3) bond is not present, the fluorescence intensity thereof was substantially the same as the fluorescence intensity of the blank sample. As a result of obtaining the ratio by dividing the fluorescence intensity of the serum of a Pca patient and the fluorescence intensity of the serum of a BPH patient by the mean or median fluorescence intensity of the blank samples of the 27 cases or the mean or median fluorescence intensity of the HLT samples of the 80 cases, the cutoff value which satisfies a detection sensitivity of 90% is as shown in Table 5, and it was found that it can be determined that when the value obtained by dividing the fluorescence intensity of the serum of a patient with suspected Pca by the mean or median fluorescence intensity of the blank samples or the mean or median fluorescence intensity of the HLT samples is higher than the cutoff value, Pca is developed or the probability of developing Pca is high, and when the value is smaller than the cutoff value, BPH is developed or the probability of developing BPH is high.

TABLE 5

(1) In the case of adopting "fluorescence intensity of serum which is analyte sample/mean fluorescence intensity of blank samples"
cutoff value: 4.975-4.990, sensitivity: 90.58%, specificity: 71.59-72.16%
(2) In the case of adopting "fluorescence intensity of serum which is analyte sample/median fluorescence intensity of blank samples"
cutoff value: 5.335-5.350, sensitivity: 90.65%, specificity: 70.79-71.35%
(3) In the case of adopting "fluorescence intensity of serum which is analyte sample/mean fluorescence intensity of HLT samples"
cutoff value: 5.260-5.300, sensitivity: 90.58%, specificity: 71.02-72.16%
(4) In the case of adopting "fluorescence intensity of serum which is analyte sample/median fluorescence intensity of HLT samples"
cutoff value: 5.565-5.600, sensitivity: 90.58%, specificity: 71.02-72.16%

INDUSTRIAL APPLICABILITY

The present invention has an industrial applicability in that a method for distinguishing between Pca and BPH with high sensitivity and good reproducibility using a small amount of an analyte sample can be provided.

The invention claimed is:

1. A method for analyzing an analyte sample, comprising:
bringing an analyte sample containing a prostate-specific antigen (PSA) into contact with a carrier having an anti-free PSA antibody immobilized thereon, thereby binding free PSA to the anti-free PSA antibody immobilized on the carrier;
thereafter bringing the carrier in which the free PSA is bound to the immobilized anti-free PSA antibody into contact with a monoclonal antibody capable of specifically recognizing galactose having a terminal sialic acid residue through an α(2,3) bond in an N-type glycan, thereby binding the monoclonal antibody to the free PSA bound to the anti-free PSA antibody immobilized on the carrier; and measuring the amount of the monoclonal antibody bound to free PSA, thereby measuring the amount of free PSA having an N-type glycan in which a terminal sialic acid residue is bound to galactose through an α(2,3) bond.

2. The method according to claim 1, wherein the analyte sample containing PSA is at least one member selected from the group consisting of serum, urine, prostatic tissue extract, semen, and bladder irrigation fluid.

3. The method according to claim 1, wherein the anti-free PSA antibody is an anti-human free PSA-specific monoclonal antibody that does not react with complexed PSA.

4. The method according to claim 1, wherein the carrier is magnetic particles.

5. A kit for distinguishing between prostate carcinoma and benign prostatic hyperplasia, comprising at least a carrier having an anti-free PSA antibody immobilized thereon and a monoclonal antibody capable of specifically recognizing galactose having a terminal sialic acid residue through an α(2,3) bond in an N-type glycan.

6. The method of claim 1, wherein the monoclonal antibody capable of specifically recognizing galactose having a terminal sialic acid residue through an α(2,3) bond in an N-type glycan is the monoclonal antibody capable of recognizing IV$^3$NeuAcnLc$_4$Cer.

* * * * *